United States Patent [19]
Collins et al.

[11] Patent Number: 6,090,057
[45] Date of Patent: Jul. 18, 2000

[54] MULTI-AXIAL EXTERNAL ORTHOTIC JOINT

[75] Inventors: Bryon E. Collins; Michael D. Morphy, both of Spokane, Wash.

[73] Assignee: Wonderful Widget Works, Ltd., Spokane, Wash.

[21] Appl. No.: 09/009,629

[22] Filed: Jan. 20, 1998

[51] Int. Cl.[7] .................................................... A61F 5/00
[52] U.S. Cl. ............................................... 602/16; 602/23
[58] Field of Search ............................. 602/16, 23, 24, 602/26, 20, 21, 27; 623/18, 39

[56] References Cited

U.S. PATENT DOCUMENTS

| | | | |
|---|---|---|---|
| Re. 33,194 | 4/1990 | Marck et al. | 602/29 |
| 3,790,965 | 2/1974 | Gelbenegger | 623/38 |
| 4,256,097 | 3/1981 | Willis | 602/16 |
| 4,677,971 | 7/1987 | Lindemann | 602/21 |
| 5,000,170 | 3/1991 | Young et al. | 602/16 |
| 5,352,190 | 10/1994 | Fischer et al. | 602/23 X |

*Primary Examiner*—Richard J. Apley
*Assistant Examiner*—Denise Pothier
*Attorney, Agent, or Firm*—Wells, St. John, Roberts, Gregory & Matkin, P.S.

[57] ABSTRACT

A multi-axial external joint used in orthoses construction to provide support and/or limit movement of various joints of the body. In combination as a complete orthosis, a foundation is provided including a girdle section and a separate thigh cuff. A first orthotic joint member is mounted to the girdle section, and a second orthotic joint member is mounted to the thigh cuff. A bearing joins the first and second orthotic joint members for pivotal movement in three dimensions about multiple intersecting axes to support articulation of a human leg about an associated hip joint including flexion, extension, abduction, adduction, and rotation of the leg. A stop assembly on at least one of the orthotic joint members enables adjustment to limit relative pivotal movement of the orthotic joint members about the pivot point.

12 Claims, 8 Drawing Sheets

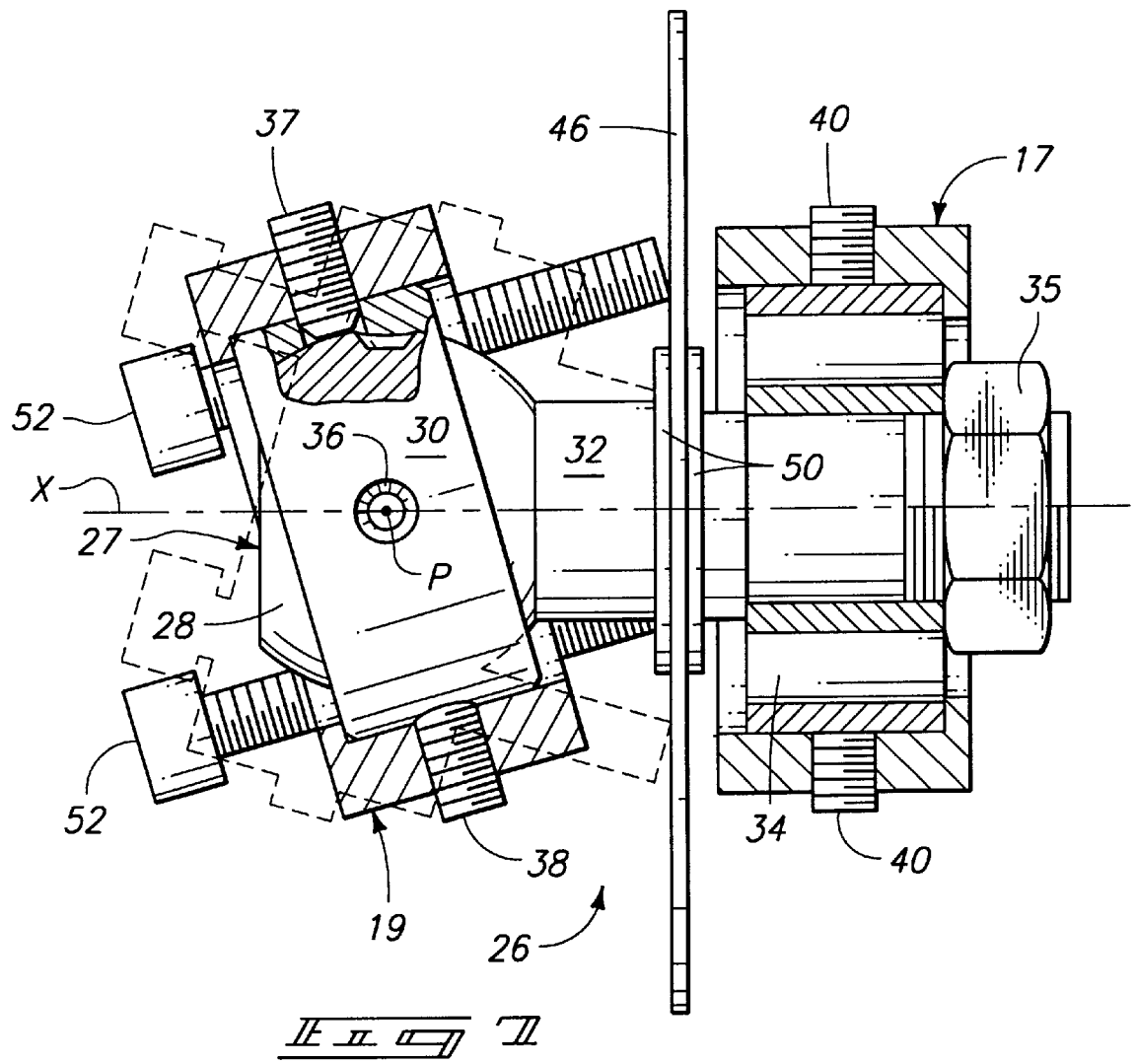

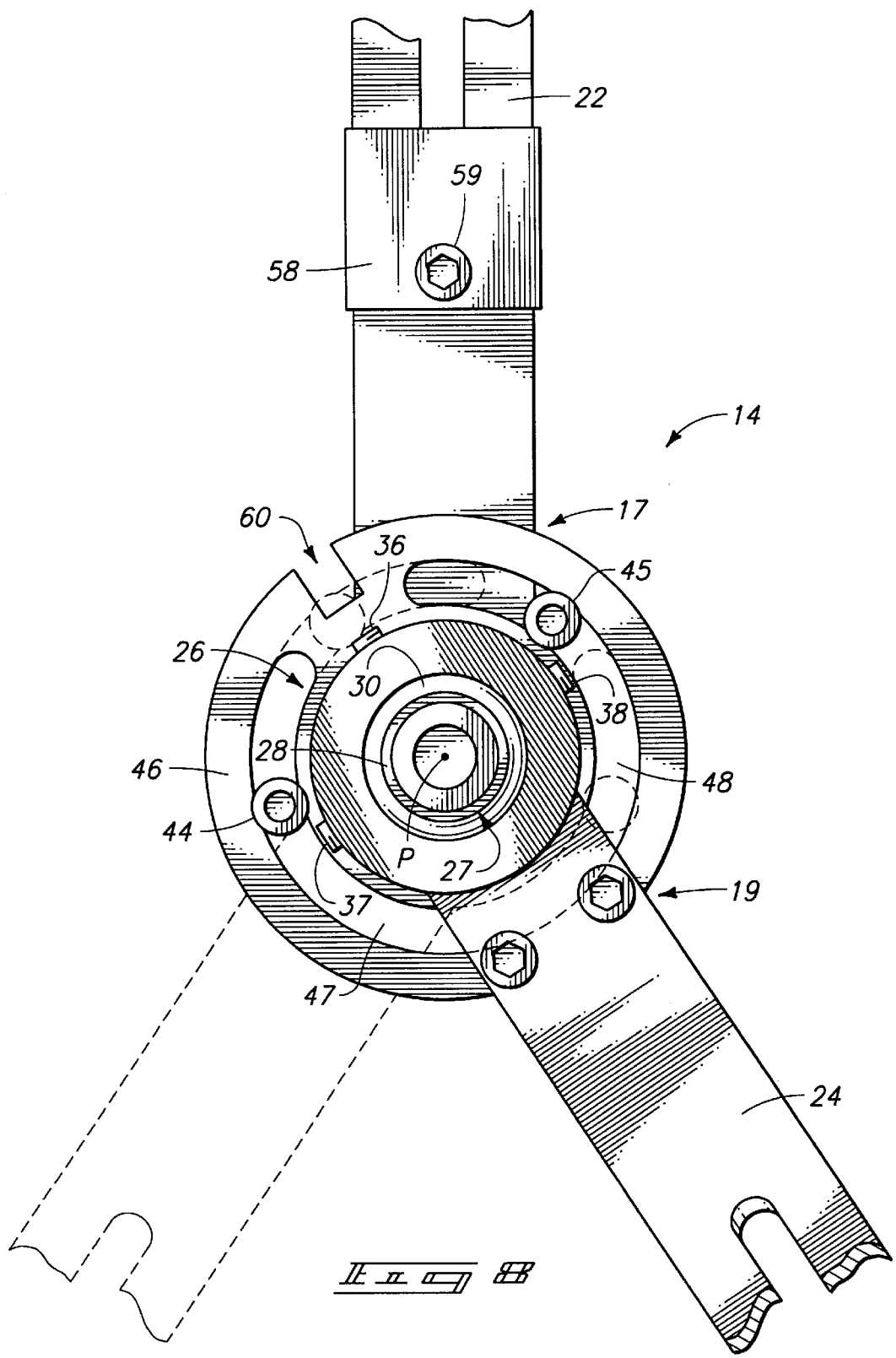

6,090,057

MULTI-AXIAL EXTERNAL ORTHOTIC JOINT

TECHNICAL FIELD

The present invention relates to the field of orthotics and more particularly to external orthotic joints.

BACKGROUND OF THE INVENTION

Various forms of external, synthetic joints have been developed in the past for limiting or assisting in joint articulation during therapy or convalescence. Such joints typically attempt to mimic the articulation of the associated joint, usually in two dimensions. Thus, all commercially available external hip joints will enable articulation of the wearer's leg through flexion and extension, but not all enable abduction and adduction. But none, to the inventors' knowledge provide for unrestricted true circumduction, a natural and desirable capability provided for in "ball" type joints such as the human hip. And none provide the abduction, adduction, flexion and extension through a single point on an axis as does the natural hip joint.

It therefor becomes desirable, for expediency in prescribing treatment, in fitting orthoses, and ultimately for effective treatment of various conditions; to obtain an external orthotic appliance that will afford adjustable, controlled three dimensional motion or traction through a single point.

The present invention therefor has for an object, provision of a multi-axial external joint that will facilitate adjustable positioning of a selected limb in three dimensions about a single point.

Another object is to provide such a joint that will enable limited movement of a selected limb in any direction about the single point.

A still further object is to provide such a joint that enables articulation of a selected limb in a manner emulating the natural articulation of an associated joint for the selected limb.

The above and still further objects and advantages will become apparent from the following detailed description which exemplifies a preferred form of the present invention.

BRIEF DESCRIPTION OF THE DRAWINGS

Preferred embodiments of the invention are described below with reference to the following accompanying drawings.

FIG. 7 is an enlarged sectional view taken substantially along line 7—7 showing rotation of the joint; and FIG. 8 is a side elevation view of the joint showing flexion and extension positions of the joint.

DETAILED DESCRIPTION OF THE PREFERRED EMBODIMENTS

Figure 1:
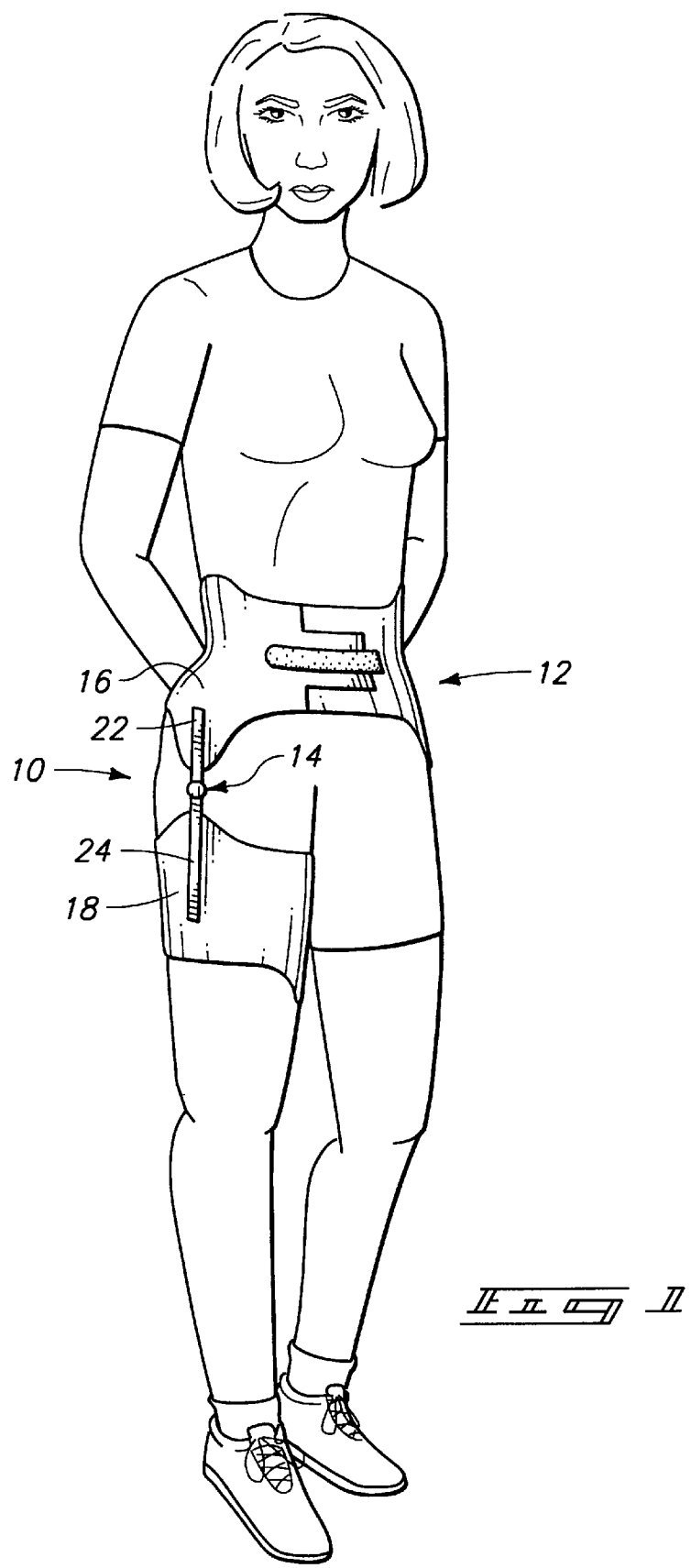
FIG. 1 is an anterior (front) view of the preferred form of the present apparatus on a person.

This disclosure of the invention is submitted in furtherance of the constitutional purposes of the U.S. Patent Laws "to promote the progress of science and useful arts" (Article 1, Section 8).

Referring in greater detail to the drawings, a presently preferred form of the apparatus is exemplified for use as an external hip orthoses 10. It should be understood, however, that alternate forms of the present joint could also be used to supplement articulation of other joints for humans or other animals without departing from the scope of the invention.

As shown, the preferred exemplary use of the present invention is with human hip orthoses which are indicated for isolated problems of the acetabular region which may result from dysplastic disorders (excessive mobility or repetitive dislocation), traumatic injury, or surgical procedures such as a total hip replacement.

The present apparatus is intended for use along with a supportive foundation 12 to secure a preferred form of the present joint 14 in spatial relation to an associated anatomic joint. In the preferred example given herein, the foundation 12 includes a first foundation member in the form of a pelvic girdle 16, and a second foundation member 18 in the form of a thigh cuff 18. The presently preferred joint 14 is mounted to the first and second foundation members and is located by such members outwardly adjacent a patient's hip joint 20.

The preferred hip orthoses 10 is shown as worn by a person about the mid section and thigh (FIGS. 1, 2) with a preferred multi-axial joint 14 (FIG. 3) connecting the two, externally of the hip joint 20. In the assembly as a hip orthoses, the foundation includes the pelvic girdle 16 and thigh cuff 18 that are advantageously constructed of high density polyethylene with hook and loop fabric closures. The pelvic girdle 16 and thigh cuff 18 are connected to proximal and distal uprights 22, 24 of the multi-axial joint 14 by standard fasteners.

Useful foundations including girdles and thigh cuffs are currently commercially available, and are shown in U.S. Pat. Nos. 5,620,412 granted Apr. 15, 1997 and 5,344,391 granted Sep. 6, 1994 and assigned to National Orthotic Laboratories Inc of Winter Haven Fla., U.S.A.

It is also pointed out that the present invention may be provided in combination with the appropriate supportive foundation 12, or individually, as an orthotic joint 14 capable of being mounted to an existing foundation.

In the example shown, a preferred orthotic joint 14 is comprised of a first orthotic joint member 17 on the first foundation member and a second orthotic joint member 19 on the second foundation member.

The orthotic joint further comprises a bearing 26 joining the first and second orthotic joint members for universal pivotal movement about a pivot point P that is positioned external to the hip joint 20. The pivot point P is situated at the intersection of multiple pivot axes defined by various components described in greater detail below.

Figure 5:
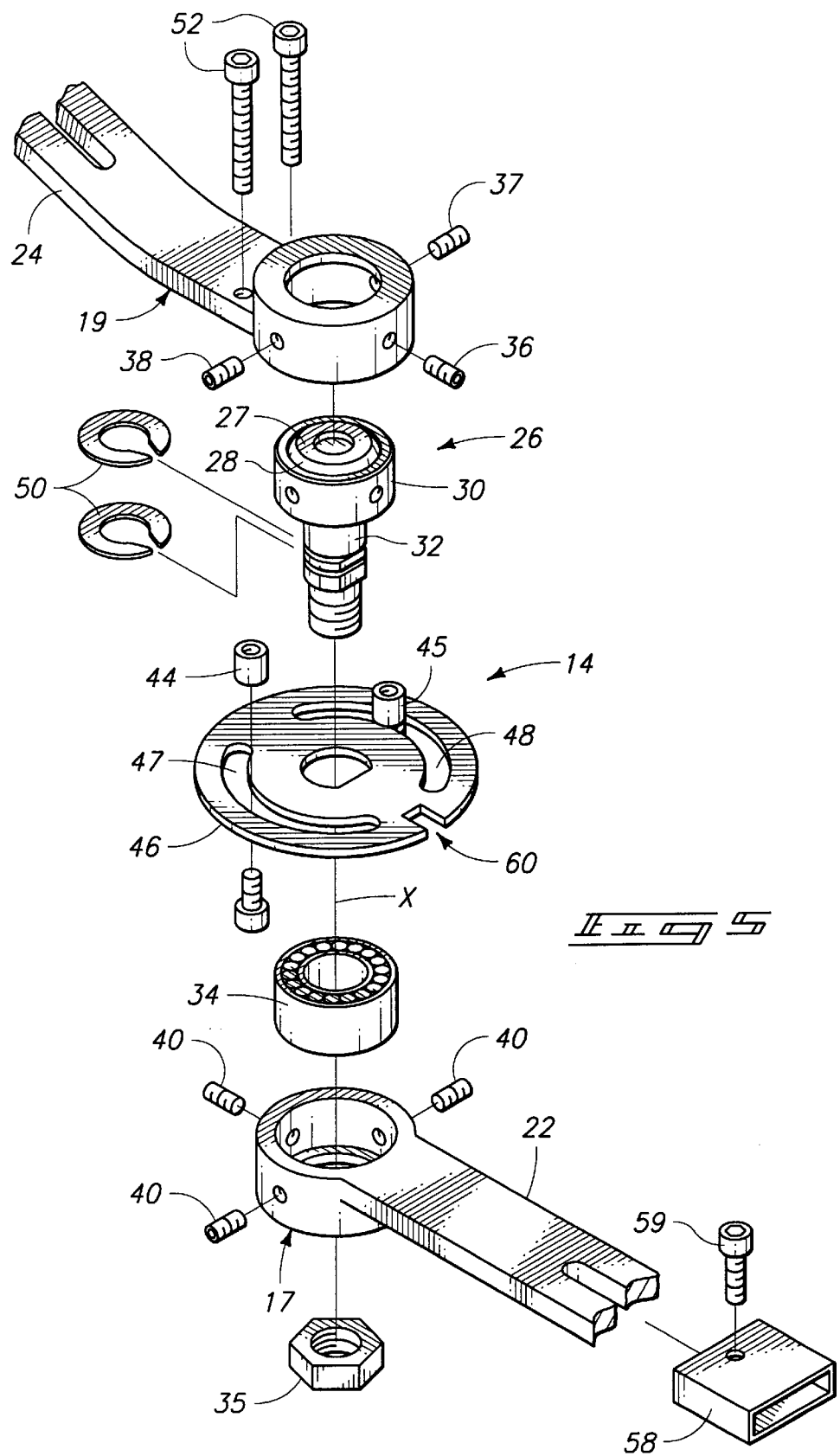
FIG. 5 is an exploded perspective view of the preferred joint with portions of the proximal and distal uprights shown fragmented.
Figure 6:
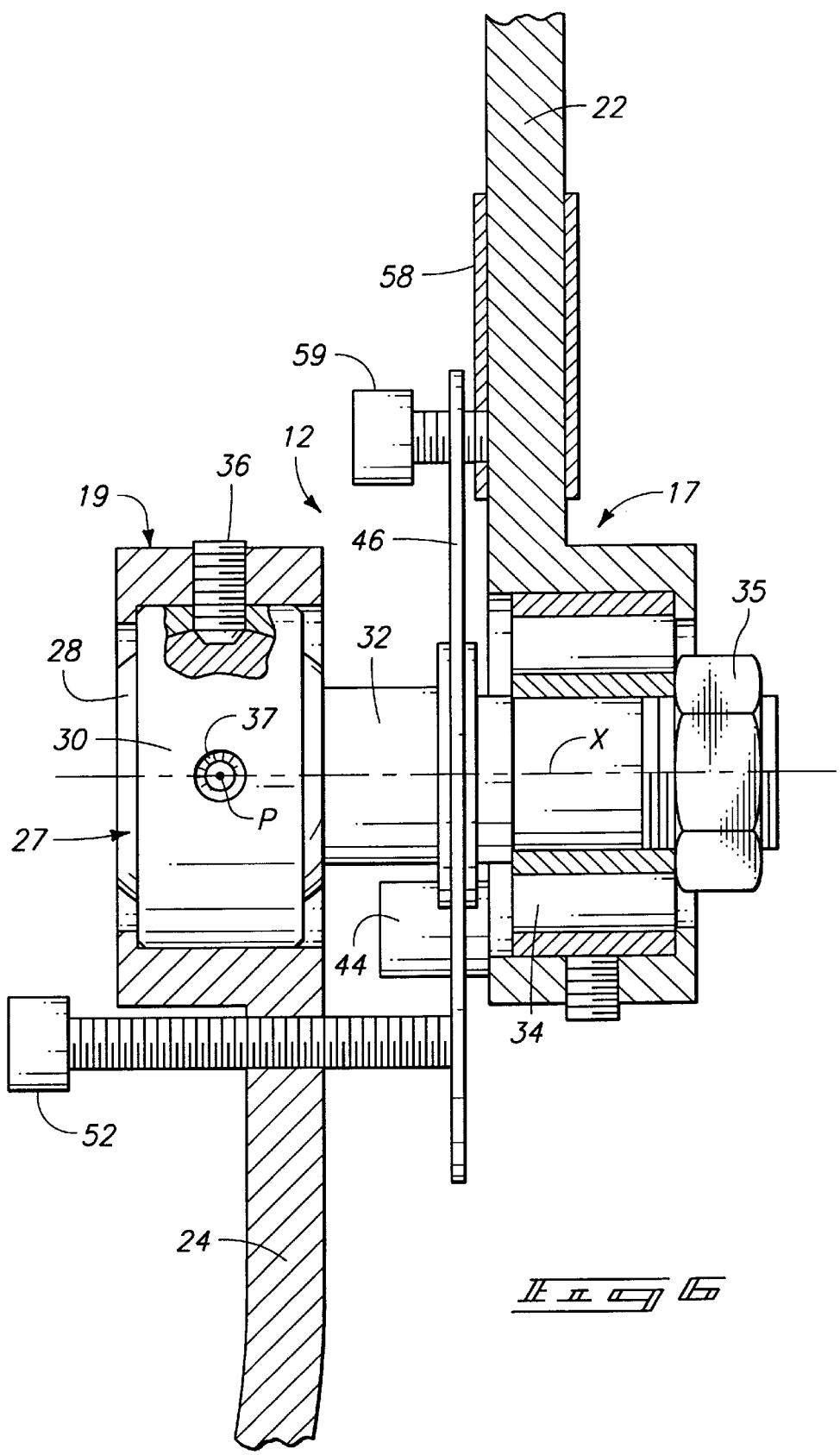
FIG. 6 is an enlarged sectional view taken through the joint.

A preferred bearing 26 is comprised of two interconnected bearings, a ball or spherical bearing 27 and an axial bearing 34. The preferred spherical bearing 27 includes a bearing head 28 that is preferably spherical with its center at point P. A race 30 (FIG. 5) is rotatably mounted to the bearing head 28. The race 30 is connected to the second orthotic joint member to permit pivotal movement of the second orthotic joint member 19 about multiple axes that intersect at point P. The race 30 on the bearing head 28 is set in the top end of the distal upright 24 of second joint member 19.

A set of three set screws 36, 37, 38 (FIGS. 5 and 6–8) extend through the distal upright 24 to engage the race 30. They may also extend through openings in the race to be selectively tightened against the bearing head 28. The set screws secure the race to the second joint member and can be selectively tightened to enable selective rotation of the race 30 and second joint member 19 about the bearing head 28.

The set screws 36, 37, and 38 are preferably angularly spaced in 90° increments about the race such that when the orthoses 10 is in place, and the uprights 22, 24 are in substantial vertical alignment (FIG. 1), the set screws 37 and 38 are aligned horizontally and the set screw 36 is oriented vertically.

The bearing head 28 (FIGS. 5–7) is integral with or affixed to a threaded shaft 32. The shaft 32 is connected by a finished jam nut 35 to the inner race of the axial bearing 34, the outer race of which is set in the bottom end of the proximal upright 22 of first joint member 17. The axial bearing 34 rotatably connects the shaft 32 and the first orthotic joint member 17 for rotation about a fixed axis X that preferably intersects point P.

Another set of set screws 40 or other appropriate fasteners secure the outer race of the axial bearing 34 to the bottom end of the proximal upright 22. These set screws are not intended to extend through the outer race and consequently do not affect angular adjustments, but simply assist in maintaining the position of the bearing 34 in relation to the proximal upright 22.

It is noted that one of the uprights (preferably the distal upright 24) is slightly angulated. This is done to accommodate abduction of the associated limb (FIG. 3) without the joint coming into contact with adjacent tissues. The bearing 26 (specifically the bearings 27, 34) enable relative pivotal motion of the proximal and distal uprights 22, 24 about the center point P of the spherical head 28 and about the axis X of the threaded shaft 32. As will be seen below, such motion is adjustably limited to enable controlled motion of associated limbs when the present orthoses 10 is mounted to a patient.

The hip orthoses embodiment is adjusted by the use of a stop arrangement including socket head screws, set screws, and standard stop screws to limit articulation of the hip as prescribed by a physician.

More specifically, an adjustable stop dial 46 is positioned axially on the shaft 32 between the bearings 27, 34. The dial 46 and shaft 32 are keyed (FIG. 5) to prevent relative rotation of the dial and shaft. Stop dial 46 is axially secured in place on the shaft by two C clip retainers 50. Two dial stops 44, 45 are adjustably secured in arcuate slots 47, 48 formed in the dial 46. The dial stops 44, 45 will come into abutment with the proximal upright 22 during flexion and extension of the distal upright. The angular amount of motion may be determined by selectively positioning the stop screws 44, 45 in the respective slots 47, 48.

The stop dial 46 is used to limit, for example hip motion, anteriorly (forward) and posteriorly (backwards), with primary motion occurring through the roller bearing 34 and proximal upright 22.

Two socket head cap screws 52 threadably extend through the distal upright 24 to enable selective and precise adjustment of the position of the distal upright 24 in abduction (away from the body to the side), internal rotation (toes together, heels apart while standing), and external rotation (toes apart, heels together while standing).

The ball joint bearing 27 is provided with adjustments to limit the distal upright 24 in both fixed (nonmoving) or limited dynamic (free moving) positions. To this end, the three set screws 36, 37, 38 on the distal upright 24 are threaded in the distal upright and can be turned to extend through holes in the outer race 30 of the ball joint bearing 27 to engage and clamp against the head 28. Two of the screws 37, 38 are diametrically opposed and can be selectively used (with the other screw 36 loosened) to limit pivotal motion of the distal upright 24 to abduction and adduction only. With the diametrically opposed screws 37, 38 loosened and the central screw 36 tightened against the head, motion of the distal upright is limited to internal and external rotation (toe in or toe out motion).

Indentations may be provided at strategic locations about the head to receive ends of the set screws 36, 37, and 38 to secure the race 30 (and distal upright 24) in predetermined positions. Alternatively, the screws may be used to secure or limit motion of the distal upright about the ball joint bearing 27 in any position (within structural limits) after the socket head cap screws 9 have been adjusted to the desired position.

A drop lock 58 is another element of the stop assembly and is slidably positioned on the proximal upright 22. The drop lock 58 includes a socket head cap screw 59 that is selectively received in a drop lock catch 60 formed in the stop dial 46. The drop lock may thus function to lock the joint fully straight, when standing, by way of the socket head cap screw 59 engaging the drop lock catch 60 of the stop dial 46. The drop lock 58 may also be locked in position along the proximal upright, clear of the stop dial to leave articulation of the joint unaffected.

The ball joint bearing 27 and axial roller bearing 34 are aligned and rotate around the same axis when the ball joint bearing 27 is set in a specific fixed position. When the ball joint bearing 27 is left to freely move through various axes, the actual motion of the hip, circumduction (in a circle), is duplicated. Reduced weight bearing through the acetabulum is also realized, while still being able to limit hip flexion and extension through adjustment of the dial stops 44, 45.

Operation of the present invention will be described by way of example relating to fitting of the present orthoses 10 on a patient with a hip disorder. Reference will be made in particular to FIGS. 1, 2, 5 and 6. Assuming a patient with post traumatic hip dislocation with closed reduction, fitting of the present orthoses will involve the following steps.

Firstly, the orthotist will measure the patient according to the circumference of the chest, waist, pelvic girdle at the anterior-superior iliac spine, greater trochanter, top of inner thigh (approximately 3 cm. from pubis) and the thigh at approximately 6 cm. above patella. Measurements are also made of the distance between the anterior-superior iliac spines and between the greater trochanters.

Figure 2:
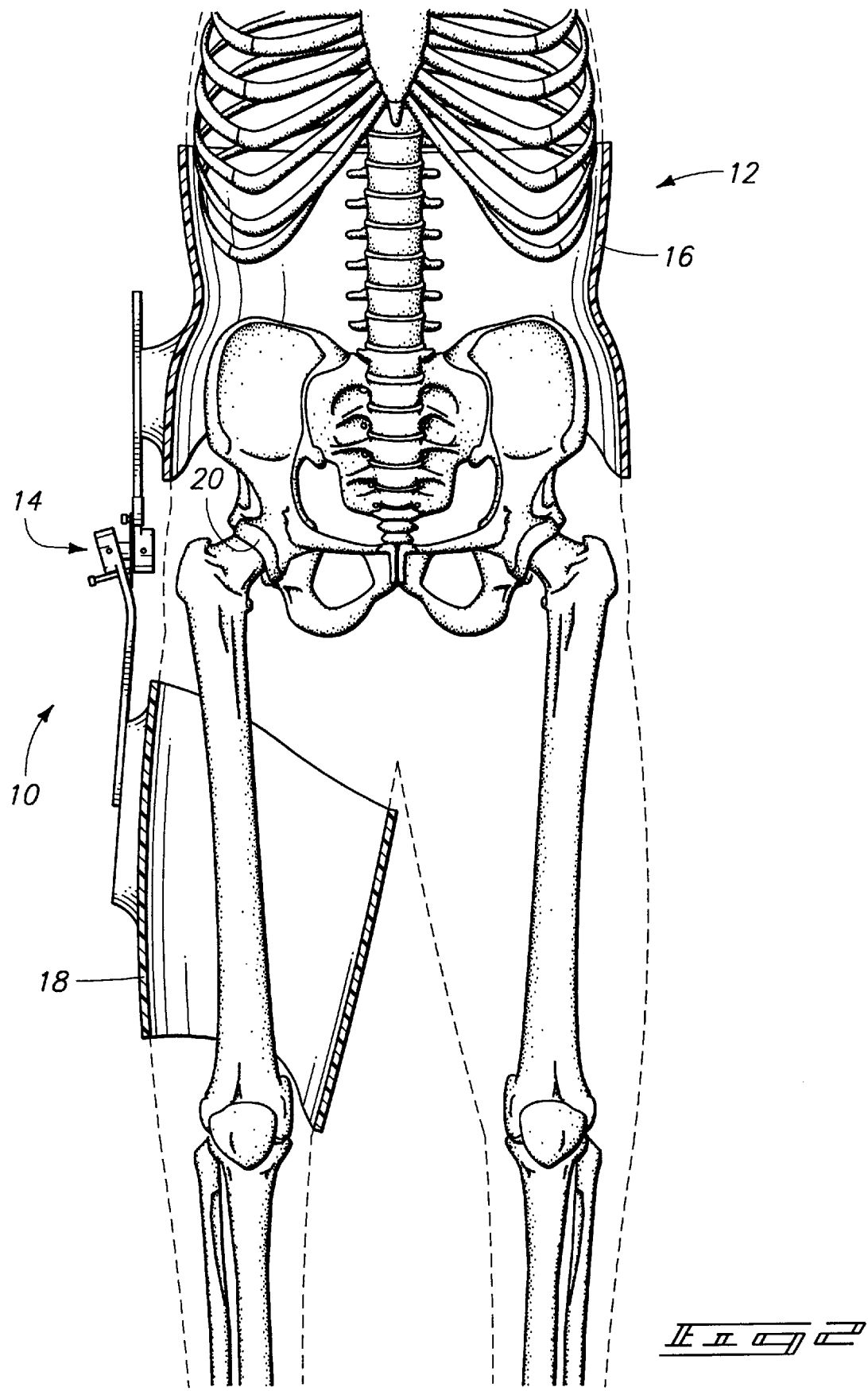
FIG. 2 is an anterior view of the preferred apparatus in medial section and showing the relationship to skeletal anatomy.
Figure 3:
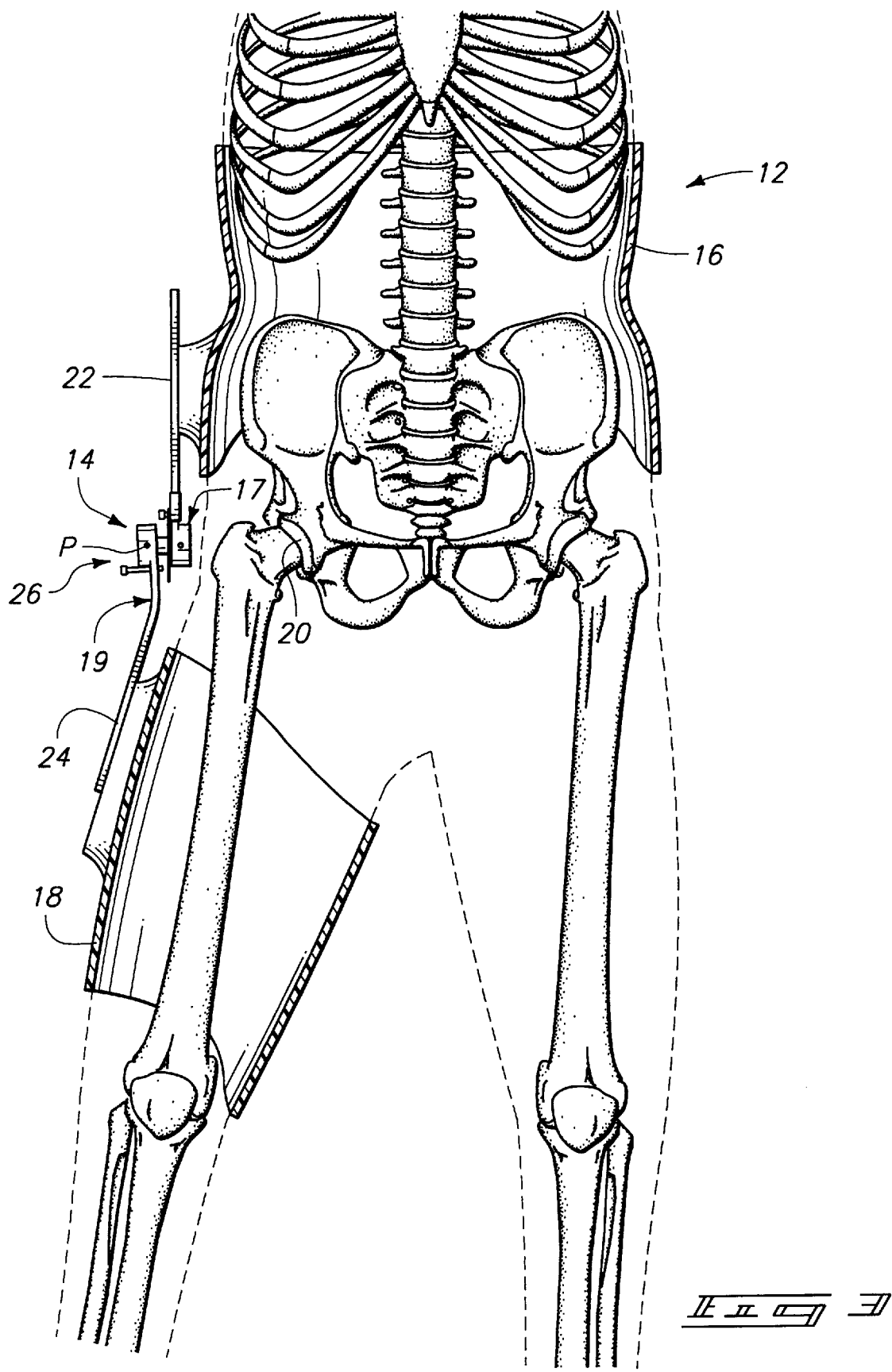
FIG. 3 is a view similar to FIG. 2 only showing the right hip joint and leg in an abducted position.
Figure 4:
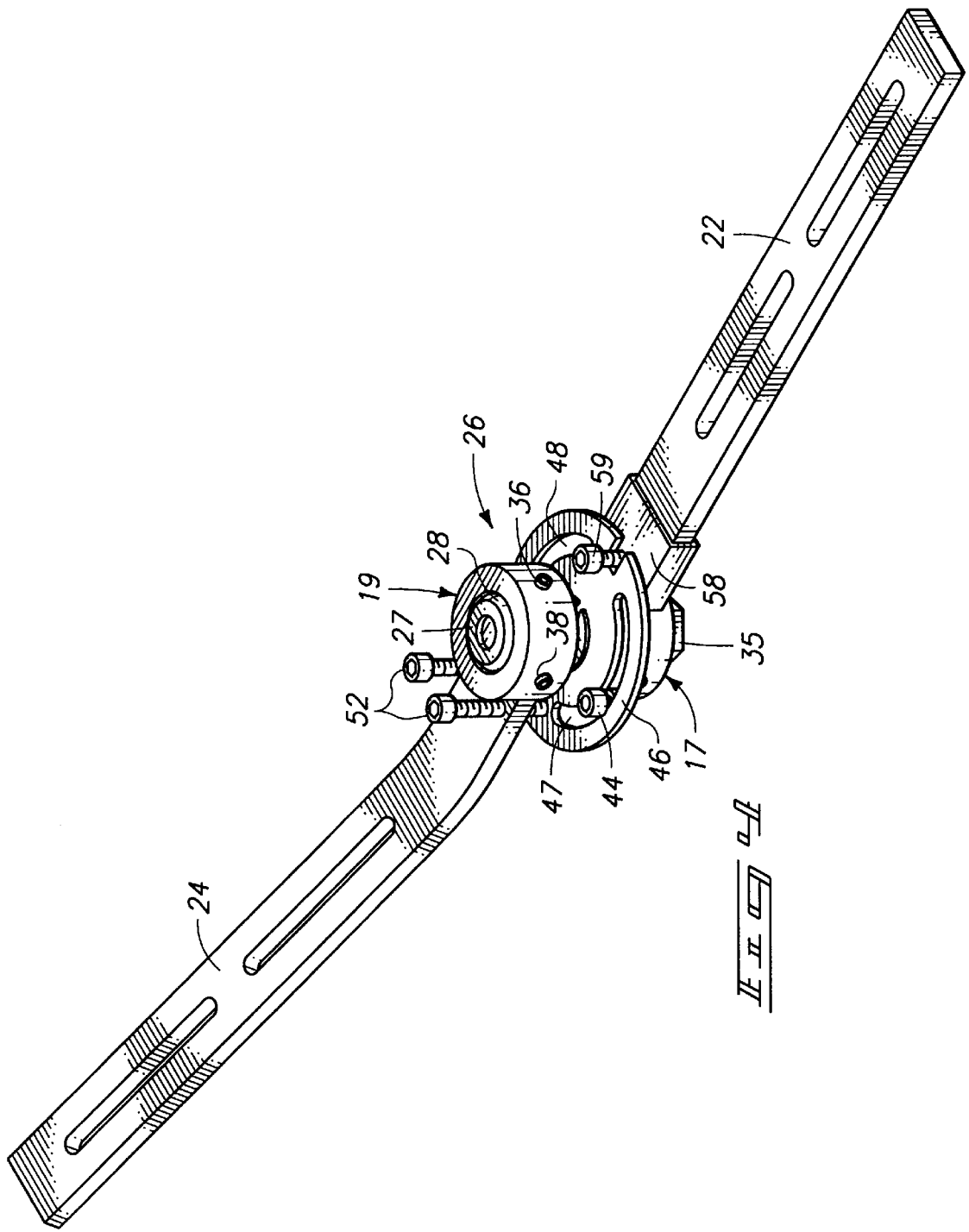
FIG. 4 is a perspective view of the preferred joint disconnected from the pelvic girdle and thigh cuff.

Next the orthotist will select an appropriate size pelvic girdle 16 and thigh cuff 18 according to the above measurements. Now the girdle and cuff are secured to the patient, with the girdle resting firmly on the iliac chest, and thigh cuff approximately 3–5 cm. from the pubis. This is best accomplished with the patient standing with weight bearing on the unaffected side (left side as shown in FIGS. 1 and 2).

Next, the orthotist will attach the joint to the pelvic girdle with the axis X (FIG. 6) in line with the greater trochanter of the hip. The proximal upright 22 is then attached to the girdle with appropriate screw fasteners. Now the distal upright 24 is similarly attached to the thigh cuff 18.

A physician's order typically will call for 7°–15° abduction of the leg at the hip joint. This is accomplished by tightening cap screws 52 until the distal upright 24 becomes 7°–15° out of parallel with the proximal upright 22. Additional active abduction by the patient may be limited by tightening set screws 36–38 at this point.

The patient's flexion is limited by adjusting the stop screw 44 in the slot 47 to a point furthest away from the drop lock notch 60 on the stop dial 46.

Hip extension is limited by adjusting the stop screw 45 in the slot 48 until it abuts the proximal upright 24 (for a 0°–90° flexion extension angle).

The drop lock 58 may or may not be used according to physician preference. If used, the socket read cap screw 59 will be loosened to allow the drop lock to slide down to engage the screw shank in the notch 60. The screw 59 will then lock the drop lock in position to prevent flexion and extension at the hip as the patient stands. The drop lock can be disengaged from the notch 60 to permit sitting. Otherwise, if the physician elects and the drop lock is not to be used, the screw 59 is used to secure the drop lock clear of the stop dial 46 and the patient is permitted free flexion and extension of her leg through the 0°–90° range selected above.

Now internal and external rotation may be adjusted by firstly backing out screws 36–38, and cap screws 52. Cap screws 52 may next be adjusted. For setting external rotation, the anterior screw is turned (against the dial 46) to rotate the distal upright 24 externally. Then the posterior screw is rotated until it touches the dial. Set screws 36–38 are then tightened. To accomplish internal rotation the cap screws 52 may be adjusted in the opposite direction.

The patient's leg is now set in the selected angular position for ambulation and healing in the optimal functional position according to the patient's anatomy.

The significantly greater adjustability of the multi-axial joint due to the use of the present bearing construction, allows for greater adjustment of hip positioning, decreased weight bearing through the acetabulum (human hip joint), and greater mobility through single point on an axis. The present joint 14 thus enables true circumduction through a single axis point when the ball joint bearing 27 is left free.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. A multi-axial external orthoses, comprising:

a foundation including a first foundation member configured to be attached to a patient to one side of an internal joint, and a second foundation member configured to be attached to a patient to an opposite side of the internal joint;

an orthotic joint mounted to the first and second foundation members between the first and second foundation members and including a first orthotic joint member on the first foundation member and a second orthotic joint member on the second foundation member;

the orthotic joint further comprising a bearing joining the first and second orthotic joint members for universal pivotal movement about a pivot point;

wherein the bearing includes a substantially spherical bearing head connected to the first orthotic joint member, and a race rotatably mounted to the spherical head and connected to the second orthotic joint member; and a stop assembly on at least one of the orthotic joint members adjustable to limit relative pivotal movement of the orthotic joint members.

2. A multi-axial external orthoses, comprising:

a foundation including a first foundation member configured to be attached to a patient to one side of an internal joint, and a second foundation member configured to be attached to a patient to an opposite side of the internal joint;

an orthotic joint mounted to the first and second foundation members between the first and second foundation members and including a first orthotic joint member on the first foundation member and a second orthotic joint member on the second foundation member;

the orthotic joint further comprising a bearing joining the first and second orthotic joint members for universal pivotal movement about a pivot point;

a stop assembly on at least one of the orthotic joint members adjustable to limit relative pivotal movement of the orthotic joint members;

wherein the bearing is comprised of a bearing head; and a race rotatably mounted to the bearing head and connected to the second orthotic joint member to permit pivotal movement of the second orthotic joint member about at least two axes that intersect at the pivot point.

3. The multi-axial external orthoses of claim 2, further comprising:

set screws positioned about the race and engageable with the bearing head to limit pivotal movement of the second orthotic joint member about at least one of said at least two axes.

4. The multi-axial external orthoses of claim 2 wherein the bearing is comprised of:

an axial bearing rotatably mounting the bearing head to the first orthotic joint member for rotation about a third axis and with a center of the bearing head being substantially coincidental with the pivot point.

5. A multi-axial external orthoses, comprising:

a foundation including a first foundation member configured to be attached to a patient to one side of an internal joint, and a second foundation member configured to be attached to a patient to an opposite side of the internal joint;

an orthotic joint mounted to the first and second foundation members between the first and second foundation members and including a first orthotic joint member on the first foundation member and a second orthotic joint member on the second foundation member;

the orthotic joint further comprising a bearing joining the first and second orthotic joint members for universal pivotal movement about a pivot point;

a stop assembly on at least one of the orthotic joint members adjustable to limit relative pivotal movement of the orthotic joint members; and wherein the bearing includes an axial bearing having an outer race mounted to the first orthotic joint member and an inner race that defines an axis;

a shaft mounted to the inner race for rotation about the axis; and a universal bearing on the shaft, mounting the second orthotic joint member for pivotal movement about the pivot point.

6. The multi-axial external orthoses of claim 5 wherein the universal bearing includes a spherical ball on the shaft, and a race freely movable about the center of the spherical ball and mounting the second orthotic joint member.

7. The multi-axial external orthoses of claim 5 wherein the universal bearing includes a spherical ball on the shaft, and a race freely movable about the center of the spherical ball and mounting the second orthotic joint member; and
wherein the center of the spherical ball is coincidental with the pivot point.

8. The multi-axial external orthoses of claim 5, wherein the stop assembly is comprised of:
a stop dial affixed to the shaft for rotation therewith; and
at least one stop on the stop dial adjustably positioned thereon to engage one of the joint members to limit relative motion of the joint members about said axis.

9. The multi-axial external orthoses of claim 5, and further comprising:
a stop dial affixed to the shaft for rotation therewith; and
a drop lock movably mounted to the first orthotic joint member to selectively engage and lock the stop dial and shaft against rotation relative to the first orthotic joint member about said axis.

10. A multi-axial orthotic joint, comprising:
a first orthotic joint member;
a second orthotic joint member;
a bearing joining the first and second orthotic joint members for pivotal movement in three dimensions about multiple axes intersecting at a pivot point to emulate articulation of a prescribed anatomical joint;
a stop assembly on at least one of the orthotic joint members adjustable to limit relative pivotal movement of the orthotic joint members about the pivot point; and
wherein the bearing includes a substantially spherical bearing head connected to the first orthotic joint member, and a race rotatably to the bearing head and connected to the second orthotic joint member.

11. A multi-axial orthotic joint comprising:
a first orthotic joint member;
a second orthotic joint member;
a bearing joining the first and second orthotic joint members for pivotal movement in three dimensions about multiple axes intersecting at a pivot point to emulate articulation of a prescribed anatomical joint;
a stop assembly on at least one of the orthotic joint members adjustable to limit relative pivotal movement of the orthotic joint members about the pivot point;
wherein the bearing includes:
a bearing head;
a race rotatably mounted to the bearing head and connected to the second orthotic joint member to permit pivotal movement of the second orthotic joint member about at least two of said axes.

12. A multi-axial hip joint, comprising:
a foundation including a girdle section and a separate thigh cuff;
a first orthotic joint member mounted to the girdle section;
a second orthotic joint member mounted to the thigh cuff;
a bearing joining the first and second orthotic joint members for pivotal movement in three dimensions about multiple axes intersecting at a pivot point to support articulation of a human leg about an associated hip joint including flexion, extension, abduction, adduction, and rotation of the leg;
a stop assembly on at least one of the orthotic joint members adjustable to limit relative pivotal movement of the orthotic joint members about the multiple intersecting axes
wherein the bearing includes an axial bearing having an outer race mounted to the first orthotic joint member and an inner race that defines one of said multiple intersecting axes;
a shaft mounted to the inner race for rotation about the one axis; and
a universal bearing on the shaft, mounting the second orthotic joint member for pivotal movement about the pivot point.

* * * * *